United States Patent
Stingl et al.

[11] Patent Number: 5,932,758
[45] Date of Patent: Aug. 3, 1999

[54] PROCESS FOR THE PRODUCTION β-AMINO-α-HYDROXYCARBOXYLIC ACIDS AND DERIVATIVES THEREOF

[75] Inventors: Klaus Stingl, Alzenau; Matthias Kottenhahn; Karlheinz Drauz, both of Freigericht, all of Germany

[73] Assignee: Degussa Aktiengesellschaft, Frankfurt, Germany

[21] Appl. No.: 09/000,627

[22] PCT Filed: Jun. 14, 1996

[86] PCT No.: PCT/EP96/02573

§ 371 Date: Jun. 1, 1998

§ 102(e) Date: Jun. 1, 1998

[87] PCT Pub. No.: WO97/02236

PCT Pub. Date: Jan. 23, 1997

[30] Foreign Application Priority Data

Jul. 4, 1995 [DE] Germany .................. 195 24 337

[51] Int. Cl.[6] .................................................. C07C 229/28
[52] U.S. Cl. ............................................. 560/39; 562/444
[58] Field of Search ................................ 560/39; 562/444

[56] References Cited

PUBLICATIONS

Kearns et al. 'Application of Yeast–Catalyzed Reductions to Synthesis of (2R, 3S)–Phenylisoserine.' Tetrahedron Letters, vol. 35, No. 18, pp. 2845–2848, 1994.

*Primary Examiner*—Gary Geist
*Assistant Examiner*—Brian J. Davis
*Attorney, Agent, or Firm*—Omri M. Behr, Esq

[57] ABSTRACT

Disclosed is a process for producing β-amino-α-hydroxycarboxylic acid derivatives of general formula (2R, 3S)- or (2S,3E)-N-(X,Y)-3-amino-2-hydroxy-3-phenyl propionic acid-Z of Formula I,

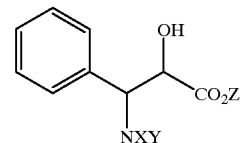

Formula 1 e.g. of (2E,3S)-3-amino-2-hydroxy-3-phenyl propionic acid or (2R,3S)-N-benzoyl-3-amino-2-hydroxy-3-phenyl propionic acid methylester. Compounds of type I are valuable intermediates in the total synthesis of Taxols which can be used in the treatment of various forms of cancer.

9 Claims, No Drawings

PROCESS FOR THE PRODUCTION β-AMINO-α-HYDROXYCARBOXYLIC ACIDS AND DERIVATIVES THEREOF

BACKGROUND OF THE INVENTION

1. Field of the Invention

The invention is directed to a new process for the production of β-Amino-α-hydroxy-carboxylic acids and derivatives of the common structure (2R,3S)- or (2S,3R)-N-(X,Y)-3-Amino-2-hydroxy-3-phenyl propionic acid-Z of the formula I

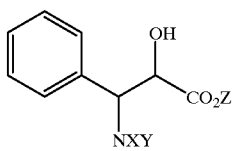

Formula 1 wherein

X H, ($C_1$–$C_6$) Alkyl, Benzyl,
Y ($C_1$–$C_6$) Alkyl, Benzyl, Formyl, $COR^1$ or $CO_2R^2$,
X,Y together Phthaloyl, Maleinoyl, or Maloneyl (sic),
$R^1$ ($C_1$–$C_6$) Alkyl, Phenyl, Benzyl, $NH_2$, 4-$NO_2$-Phenyl or 4-$NO_2$-Benzyl,
$R^2$ ($C_1$–$C_6$) Alkyl, Phenyl, Benzyl, 4-$NO_2$-Phenyl or 4-$NO_2$-Benzyl,
Z H, ($C_1$–C5) Alkyl, Phenyl, Benzyl, 4-$NO_2$-Benzyl, 4-$NO_2$-Phenyl or Allyl 2. Discussion of the Prior Art Compounds of Type I are useful intermediates in the total synthesis of Taxol (Paclitaxel), which finds use in the treatment of different types of cancer. A compound (2R,3S)-Benzoyl-3-amino-2-hydroxy-3-phenylpropionyl-methylester of Formula II falling under Formula I

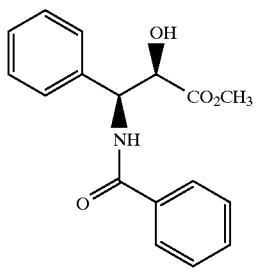

Formula II is for example described in Tetrahedron Letters 35, 2845 (1994) as similarly derived from optically active Phenyl glycine and also as a key step in the enzymatic reduction of an α-Keto ester. A substantial disadvantage of the synthetic method is that the compound of Formula II can only be isolated in 12% yield. Task of the present invention therefore is to provide a process which delivers higher yields and proceeds in an environmentally friendly and economical manner.

SUMMARY OF THE INVENTION

The process in accordance with the invention runs from
a) (S)- or (R)-Phenyl glycine of Formula III

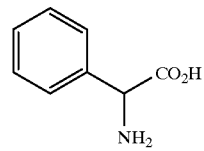

Formula III as starting material. This is reduced with a Hydride reagent.
Suitable Hydride reagents are Lithium aluminum hydride or Sodium borohydride/Activator.

b) The (S) or (R)-Phenyl glycinol of Formula IV obtained in Step (a)

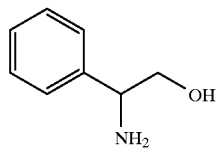

Formula IV is then
c) converted into N-protected β-Amino alcohol (S)- or (R)-N-(X,Y)-Phenyl-glycinol of general Formula V

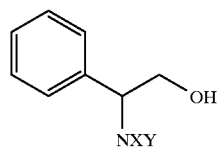

Formula V wherein
X H, ($C_1$–$C_6$) Alkyl, Benzyl,
Y ($C_1$–$C_6$) Alkyl, Benzyl, Formyl, $COR^1$ or $CO_2R^2$,
X,Y together Phthaloyl, Maleinoyl, or Maloneyl (sic),
$R^1$ ($C_1$–$C_6$) Alkyl, Phenyl, Benzyl, $NH_2$, 4-$NO_2$-Phenyl or 4-$NO_2$-Benzyl,
$R^2$ ($C_1$–$C_6$) Alkyl, Phenyl, Benzyl, 4-$NO_2$-Phenyl or 4-$NO_2$-Benzyl.

This temporary blocking of the reactive Amino groups before the subsequent oxidation of the Hydroxyl group is essential to its preservation and proceeds as is described in detail later.

d) By the oxidation of the compound of Formula V a (S)- or (R)-N-(X,Y)-Phenyl glycinal of Formula VI is obtained.

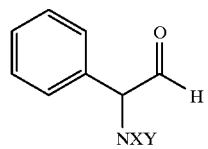

Formula VI the oxidation, wherein X and Y have the above-mentioned values proceeds as will be described in detail below.
Subsequently the compound of Formula VI e) is converted to (1RS,2S)- or (1RS,2R)-2-(X,Y)-Amino-1-cyano-2-phenylethan-1-ol of Formula VII

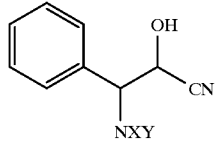

Formula VII wherein X and Y have the above-mentioned values. The formation of the nitrile may take place by means of well known procedures.

f) The thus obtained nitrile (Formula VII) is hydrolyzed to the acids VIII+IX or also their addition salts of Formulas X and XI

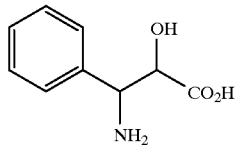

Formula VIII

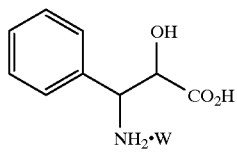

Formula XI

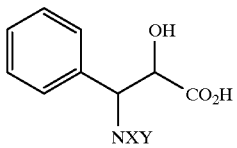

Formula IX

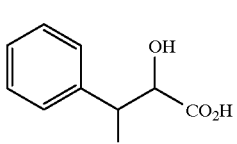

Formula X

wherein X and Y have the above-given values and W represents HC, HBr or $H_2SO_4$. The hydrolysis carried out in the manner set forth in detail below.

g) Subsequently the compounds of Formulae VIII and XI are converted in accordance with usual methods to (2RS, 3S)- or (2RS,3R)-3-Amino-2-hydroxy-3-phenyl propionic acid esters of Formula XII

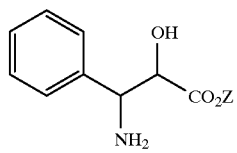

Formula XII wherein Z is ($C_1$–$C_6$) Alkyl, Phenyl, Benzyl, 4-$NO_2$-Phenyl, 4-$NO_2$-Benzyl or Allyl, and i) Subsequently the still free nitrogen function of Formula X is protected by likewise known methods

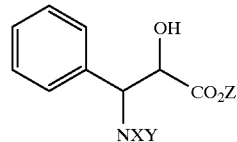

Formula I wherein Z, X and Y have the above-identified values, or k) compounds IX and X are converted to the compounds of Formula I in accordance with the procedures of g).

DESCRIPTION OF THE PREFERRED EMBODIMENTS (S)- or (R)-Phenyl glycinol V are obtained by generally known methods in which the acid function of, for example, (S)-Phenyl glycine III is treated with hydride reagents as in JP-OS-5-221935 such as, for example, Lithium aluminum hydride or sodium borohydride/activator, preferred is the system sodium borohydride/sulfuric acid to reduce it to (S)-Phenyl glycinol IV.

The blocking of the nitrogen function of the β-Amino alcohol (R)- or (S)-Phenyl glycinol V is similarly carried out in a generally known manner (analogous Synth. Commun. 1995, 25, S. 561). Thus for example, the reaction solution of the previous reaction step is reacted at pH 6–12, preferably pH 7–8.5, and 0–15° C. with for example a chloroformic acid-lower alkylester. The compound may be purified by crystallization from, for example, toluene, in which the carbamoylated β-Amino alcohol is extracted into hot toluene from the alkaline reaction solution.

The oxidation of the protected amino alcohol V to the corresponding N-blocked Aminoaldehyde VI is similarly carried out in accordance with generally known methods (analogous Tetrahedron Letters 33, 5029 (1992)). For this precursor V is converted into the aminoaldehyde with the help of TEMPO (2,2,6,6-Tetramethylpiperidin-1-oxyl) in the presence of hypochlorite solution [NaOCl or NaOBr (generated from NaOCl and KBr)]. In this reaction there are utilized amounts of nitroxyl radical (TEMPO) in the region of 0.05–10 mol %, suitably 0.5–2 mol % and 1–4 equivalents, suitably 1.2 equivalents of hydrochlorite solution [(NaOCl or NaOBr) generated from NaOCl and KBr, normally 12–13%]. Both of these reagents are readily processable in technical quantities and are commercially available. Since for the utilization of the oxidation system the presence of hypochloric acid or hypobromic acid are required, these are generated in situ from technical bleach solution or technical bleach solution and KBr by the reduction of the pH value with acid or a pH value reducing base advantageously, for example, sodium-bicarbonate. The oxidation reaction proceeds at temperatures between −30–15° C., particularly advantageously between −20 and −10° C. very effectively, in a two-phase system. As suitable solvents all inert organic solvent materials were basically found suitable. In particular however, halogenated hydrocarbons, for example dichloromethane, chloroform, 1,1,1-Trichloroethane or also the esters of formic acid and acetic acid are advantageous. In order to destroy the excess hypochoric acid workup is carried out with a reducing agent such as sodium thiosulfate solution. This oxidation step is free of heavy metals and is thus considered a particularly environmentally friendly step.

For formation of the nitrile of Formula VI in a generally known manner, a solution of the aminoaldehyde VI in an inert organic solvent preferably in toluene, dichloromethane, or ethyl acetate is reacted with 1–5 equivalents of hydrogen cyanide advantageously 1–1.3 equivalents with the addition of 10–0.01 mol % of a base, preferably 0.1–0.05 mol % of a tertiary organic nitrogen base such as, for example, Triethylamine, N-Methylmorpholine or Tributylamine, at temperatures between 0 and +35° C., suitably at +15° C. Surprisingly the hydrogen cyanide addition runs with unexpectedly high stereo selectivity. In a reaction of (S)-Phenylglycine one observes a diastereo selectivity of (1R, 2S):(1S,2S) of between 65:35 up to >74:26.

The hydrolysis of the cyanohydrin VII with an inorganic acid, for example a 21% hydrochloric acid under reflux temperature to yield the hydroxy amino acids VIII and XI results similarly in a generally known manner (analog Liebigs Annalen der Chemie 749, 198 (1971)). In order to remove the cracking products obtained during the hydrolysis, it is advantageous to wash the hydrochloric acid solution with toluene or with another solvent which is inert under these conditions. In order to isolate the compounds of the general formula VIII, the pH subsequently must be brought to a value of between 4–8, preferably 6.5–7, with the assistance of an inorganic base such as, for example, NaOH, KOH, NaHCO$_3$, or Na$_2$CO$_3$. Within the framework of the invention, it was demonstrated under these conditions the simultaneous dissociation of the protecting group which is advantageous for the further synthetic steps. In principle, there should also be considered the utilization of N-protecting groups which, under the conditions of CN-Hydrolysis directly yield compounds of the general formula I wherein Z=H (Formulas IX and X).

It has further been found that an intermediate isolation of XI as hydrochloride by simple concentration of the hydrochloric acid reaction solution yields in addition to high chemical purity an unexpectedly high diastereomeric purity [under utilization of (S)-Phenylglycine (2R,3S):(2S,3S) in a ratio of 90:10 to >95:5]. Similarly the acid VIII is obtained from the hydrochloric acid reaction solution by raising of the pH to 4–8, suitably 6.5–7 at a similarly high chemical as well as diastereomeric purity [in a reaction with (S)-Phenylglycine dr (2E,3S):(2S,3S) of between 90:10 up to >95:5].

The ester formation is carried out in accordance with generally known methods in the presence of 1.1–4 equivalents of an inorganic acid, suitably with 1.1 equivalents of sulfuric acid.

The benzoylation of, for example, a methyl ester of Formula XII, wherein Z=CH$_3$ proceeds in a generally known manner in that an aqueous solution or suspension of the ester XII buffered with sodium bicarbonate, is reacted with benzoyl chloride at a temperature of between +5 to +15° C.

In another variation the N-protected α-hydroxy acid IX is produced thereby that a) the (2RS,3S) or (2RS,3R)-3-Amino-2-hydroxy-2-phenyl-propionic acid of Formula VIII

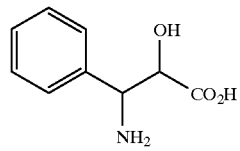

Formula VIII is first converted with a protecting group reagent into the N-protected form of Formula IX

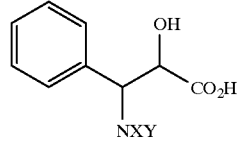

Formula IX wherein X and Y have the above-identified meaning, b) and is converted to an ester of Formula I with an esterification agent

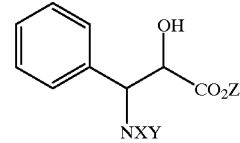

Formula 1 wherein Y and Z have the above-identified meaning.

A benzoylation of, for example (2RS,3S)-2-Amino-3-hydroxy-2-phenyl-propionic acid VIII proceeds in a generally known manner in that an aqueous solution or suspension of the acid VIII is reacted under the addition of a base, for example an inorganic base such as NaOH, KOH, NaHCO$_3$, or Na$_2$CO3, or an organic base such as triethylamine or N-Methyl morpholine at a temperature of from +5–+15° C., advantageously at +5° C. and a pH range of 6–12, advantageously at pH=9 with benzoyl chloride.

The esterification of for example a benzoylated α-hydroxy acid IX (R$^1$=H, R$^2$=COR$^3$ and R$^3$=Phenyl) is suitably carried out in the presence of catalytic amount of an acid such as for example sulfuric acid under heating, for example up to reflux temperature.

EXPERIMENTAL

The following Examples should illustrate the present invention but should in no way be considered to limit it. All temperatures are set forth in ° C.

EXAMPLE 1

(S)-N-Methoxycarbonyl-phenyl glycinol

To a suspension of 75.6 g (0.5 mol) (S)-Phenylglycine and 47.5 g NaHB$_4$ in 750 mol DME (dimethoxyethane) at a temperature of +5° C. a solution of 33 ml (0.625 mol) of concentrated H$_2$SO$_4$ in 120 ml DME is added over the space of about 1 hour so that the temperature does not exceed 10° C. At the end of the addition the mixture is permitted to rise to room temperature and carefully heated under reflux for 2 hours. Subsequently approximately ¾ of the solvent material is distilled off, the reaction mixture quenched with 100 ml MeOH, 200 ml $H_2O$ and 50 ml of concentrated HCl in this sequence at between +10 and +30° C. 50% NaOH is added to adjust the pH to 8 and 42.3 ml (0.55 mol) of methyl chloroformate is added dropwise at +5° C. so that a temperature of +15° C. is not exceeded. During this, the pH is held at between 7.5 and 8 by the addition of 50% NaOH and the mixture stirred for approximately 1 hour after the addition of the carbamoylation material. Subsequently there is added 500 ml of toluene warmed to +50° C., the phases separated and the alkaline phase again extracted at the above mentioned temperature with 300 ml of toluene. The combined organic extracts are concentrated to 200 ml and the precipitated product is dried at 50° C. in a vacuum drying chamber.

Yield: 76.2 g (78%),

Purity: >95% via $^1$H-NMR, (sic)

Melting Point: 102–105° C.,

C10H12NO3: calculated C 61.53 H 6.71 N 7.17; found C 61.62 H 6.93 N 7.34.

EXAMPLE 2

(S)-N-Ethoxycarbonyl-phenylglycinol

Procedure of synthesis and quantities analogous to Example 1. As Carbamoylating reagent there is now utilized ethyl chloroformate.

Yield: 89.0 g (85%),

Purity: >95% via $^1$H-NMR,

Melting Point: 90–93° C.,

C11H15NO3: calculated C 63.14 H 7.23 N 6.69; found C 63.19 H 7.43 N 7.05.

EXAMPLE 3

(2RS,3S)-3-Amino-2-hydroxy-3-phenylpropionic acid

To a suspension of 180.2 g (861 mmol) (S)-N-Ethoxycarbonyl-phenylglycinol in 1.5 | of ethyl acetate cooled to –17° C., there is added 10 g (84 mmol) KBr and 235 mg (1.5 mmol) TEMPO (2,2,6,6-Tetramethylpiperidin-1-oxyl). To this is added a solution of NaOCl adjusted to pH 8.9–9.2 [665 g technical NaOCl (12–13%), 400 ml $H_2O$ and ca. 115 g $NaHCO_3$)] within a space of 3 hours, in such a way that a temperature of –12° C. is not exceeded. After addition of 350 ml of a 5% sodium thiosulfate solution and 100 ml of water the phases are separated and the aqueous phase extracted once with 500 ml of acetic acid ethyl acetate. The combined organic extracts are washed once with 400 ml of saturated sodium bicarbonate solution and 200 ml of water. After drying with $MgSO_4$ 70 mg (0.7 mmol) of triethylamine are added, cooled to +15° C. and 31 ml (800 mmol) hydrogen cyanide are added dropwise so that the temperature of +25° C. is not exceeded. After completion of the addition, stirring is continued for a further 2 hours. Thereafter, there is added to the reaction solution 1.3 liters of a 21% aqueous hydrochloric acid solution, the acetic acid ethyl ester stripped off and heating continued under reflux for 16 hours, the hydrochloric acid solution is cooled to room temperature and extracted once with 300 ml of toluene. Subsequently the hydrochloric acid solution is concentrated to volume of ca. 300 ml and brought to a pH value of 6.8 at a temperature between +15–25° C. with 40% NaOH. The mixture is cooled to 5° C. and the precipitated product vacuum filtered, washed with 200 ml of cold water and dried at 50° C. in a vacuum drying chamber. The product is thus obtained in the form of a yellow solid.

Yield: 90 g, including 33% NaCl, that is to say 60.3 g (39%),

Purity: 94% after HPLC, dr [(2R,3S):(2S,3S)]: 92:8 per HPLC determination.

EXAMPLE 4

(2R,3S)-N-Benzoyl-3-amino-2-hydroxy-3-phenylpropionic acid methyl ester

To a suspension of 15.0 g (55.5 mmol, thus only 67%) (2RS,3S)-2-Amino-3-hydroxy-2-phenylpropionic acid (from Example 3) in 250 ml methanol one carefully adds dropwise at room temperature 5 ml of concentrated $H_2SO_4$ and heated for 6 hours under reflux. 50 ml $H_2O$ are added and the pH adjusted to 6.8 with 50% NaOH at +5° C. Subsequently the methanol is removed by vacuum distillation, the mixture cooled to +5° C. and reacted with 10 g (120 mmol) $NaHCO_3$ and 8.4 ml (72 mmol) benzoylchloride are added dropwise over 20 minutes. After further stirring for 2 hours the precipitated raw product is vacuum filtered, recrystallized out of 150 ml of methanol and dried to a colorless product at 50° C. in a vacuum drying vessel.

Yield: 12.1 g (73%),

Purity: >99% after HPLC,

Melting Point: 162–168° C.

dr [(2R,3S):(2S,3S)]: >95% per HPLC and $^1$H-NMR.

EXAMPLE 5

(2R,3S)-3-Amino-2-hydroxy-3-phenyl propionic acid-hydrochloride

To 60 ml of a 1 molar solution of (1RS,2S)-N-Methoxycarbonyl-2-amino-1-cyano-phenylethan-1-ol in dichloromethane there are added 160 ml concentrated HCl and the dichloromethane distilled off. Subsequently the solution is heated for 10 hours under reflux, the reaction solution cooled to room temperature and extracted once with 50 ml of toluene. After concentration of the hydrochloric acid solution to circa 30–40 ml the precipitated solid is vacuum filtered, washed with ether and dried at 50° C. in a vacuum drying chamber.

Yield: 1.9 g (15%).

Purity: >95% after $^1$H-NMR.

dr [(2R,3S):(2S,3S)]: >95:5 after $^1$H-NMR.

EXAMPLE 6

(2R,3S)-N-Benzoyl-3-amino-2-hydroxy-3-phenylpropionic acid methyl ester 1.50 g ((2R,3S)-2-Amino-3-hydroxy-2-phenylpropionic acid hydrochloride (from Example 5) are dissolved in 80 ml of a 1:1 mixture of $H_2O$/toluene and reacted at a pH value of 9.0 with 0.93 ml (8 mmol) benzoylchloride wherein the pH is maintained by the addition of 30% NaOH. After completion of the reaction the phases are separated, the alkaline phase is extracted once with 50 ml of toluene and subsequently brought to pH 2.0 at 5° C. with 2N HCl. The thus precipitated solid is removed by vacuum filtration and co-evaporated with 100 ml of toluene. This is then dissolved in 80 ml MeOH, reacted with 0.1 ml concentrated $H_2SO_4$ and heated for 4 hours under reflux.

After concentration to ca. 10 ml and dilution with 30 ml diethyl-ether, the precipitated colorless product is vacuum filtered and dried at 50° C. in a vacuum drying chamber.

Yield: 1.54g (75%).

Purity: >95% after HPLC.

dr [(2R,3S):(2S,3S)]: >95 after $^1$H-NMR.

General working procedure for the synthesis of (1RS:2S)-N-ethoxycarbonyl-2-amino-1-cyano-2-phenylethan-1-ol (Diastereomeric relationship in dependence upon the utilized solvent, Examples 1–7):

To a solution of 32 ml of a 10% aldehyde solution (15.4 mmol) and 10 mg (0.1 mmol) triethylamine 0.66 ml (17 mmol) of HCN are added dropwise at 15° C. over 10 minutes, and stirred for 30 minutes to 1 hour. Subsequently the conversion and the diastereomeric relationship (dr value) are determined by HPLC.

EXAMPLE 7

Solvent material: dichloromethane

Conversion: quantitative dr [1R,2S):(1S:2S)]: 69:31

EXAMPLE 8

Solvent material: toluene

Conversion: quantitative dr [1R,2S):(1S:2S)]: 73:27

EXAMPLE 9

Solvent material: acetic acid ethylester

Conversion: quantitative dr [1R,2S):(1S:2S)]: 74:26

We claim:

1. A process for the production of β-Amino-α-hydroxy-carboxylic compounds of the common structure (2R,3S)- or (2S,3R)-N-(X,Y)-3-Amino-2-hydroxy-3-phenyl propionyl —Z of the formula I

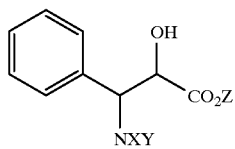

Formula I wherein
X is H, $(C_1-C_6)$ Alkyl, Benzyl,
Y is $(C_1-C_6)$ Alkyl, Benzyl, Formyl, $COR^1$ or $CO_2R^2$,
X,Y taken together are Phthaloyl, Maleinoyl, or Malonyl,
$R^1$ is $(C_1-C_6)$ Alkyl, Phenyl, Benzyl, $NH_2$, $4-NO_2$-Phenyl or $4-NO_2$-Benzyl,
$R^2$ is $(C_1-C_6)$ Alkyl, Phenyl, Benzyl, $4-NO_2$-Phenyl or $4-NO_2$-Benzyl,
Z is H, $(C_1-C_5)$ Alkyl, Phenyl, Benzyl, $4NO_2$-Benzyl, $4NO_2$-Phenyl or Allyl comprising the sequential steps of a) reducing a (S)- or (R)-Phenyl glycine of Formula III

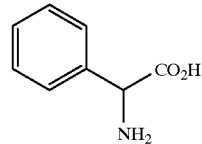

Formula III with a Hydride reagent, b) reacting the thus obtained (S) or (R)-Phenyl glycinol of Formula IV

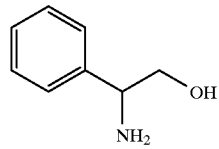

Formula IV with an XY-primary amine protecting agent to provide an

N-protected β-Amino alcohol (S)- or (R)-N-(X,Y)-Phenyl-glycinol of general Formula V

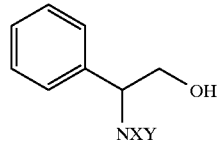

Formula V c) the compound of Formula V is oxidized to give a (S)- or (R)-N-(X,Y)-Phenyl glycinal of Formula VI

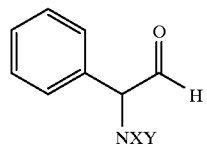

Formula VI e) which is then reacted with cyanide ions to yield (1RS,2S)- or (1RS,2R)-2-(X,Y)-Amino-1-cyano-2-phenylethan-1-ol of Formula VII

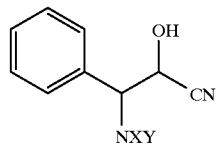

Formula VII f) the thus obtained cyanohydrin (Formula VII) is hydrolyzed with an inorganic acid selected from the group consisting of HCl, HBr and $H_2SO_4$ to yield the acids VIII+IX and their addition salts of Formulas X and XI Formula VIII

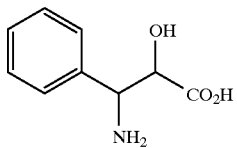

Formula XI

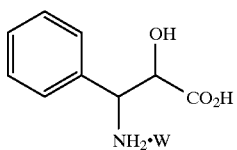

Formula IX

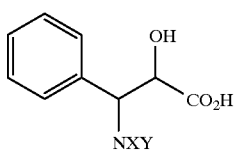

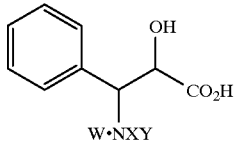

wherein W represents HCl, HBr or $H_2SO_4$, g) isolating the compounds of the formulae VIII and XI from the reaction mixture reacting the compounds of Formulae VIII and XI with ZOH to yield (2RS,3S)- or (2RS,3R)-3-Amino-2-hydroxy-3-phenyl propionic acid esters of Formula XII Formula XII

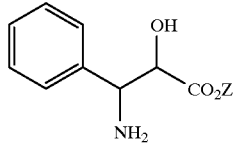

wherein Z is ($C_1$–$C_6$) Alkyl, Phenyl, Benzyl, 4-$NO_2$-Phenyl, 4-$NO_2$-Benzyl or Allyl, and h) the still free nitrogen function of Formula XII is reacted with an XY-primary amine protecting agent to yield.

Formula I

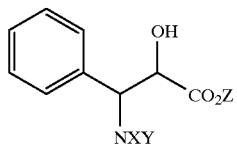

2. Process in accordance with claim 1, wherein the oxudation is performed with 2,2,6,-tetramethyl piperidine-1-oxyl in the presence of aqueous hypo-chlorite solution.

3. Process in accordance with claim 1, wherein the cyanation of the aminoaldehyde is performed with hydrogen cyanide in the presence of a tertiary nitrogenous base.

4. Process in accordance with claim 3 wherein the nitrogenous base is triethylamine in the range of 0.1–0.05 mol %.

5. Process in accordance with claim 1, wherein the formation of a cyanohydrin of general Formula VII Formula VII

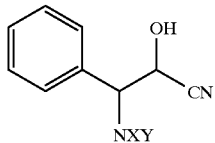

results from the reaction of the corresponding aminoaldehyde VI in the presence of an organic solvent under the addition of hydrogen cyanide and a base, with diastereo selectivity of >74:26.

6. Process in accordance with claim 1, wherein the hydroxy amino acid of general Formula XI Formula XI

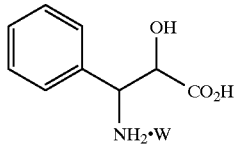

Formula VIII

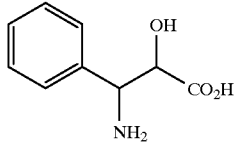

wherein W=HCl is produced in a diastereo selectivity of >95:5, after hydrolysis of the corresponding cyanohydrin of Formula VII followed by concentration.

7. Process in accordance with claim 1 wherein the compounds IX and X are reacted with ZOH to yield compounds of Formula I.

8. The process of claim 3 wherein the nitrogenous base is 10–0.01 mol % of triethylamine.

9. Process in accordance with claim 1, wherein the hydroxy amino acid of Formula VIII Formula VIII

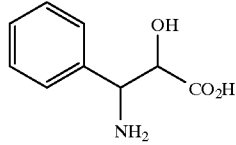

is produced in a diastereo selectivity of >95:5, and is brought to a pH value of 4–8.

* * * * *